United States Patent
Israelsson et al.

(10) Patent No.: US 10,936,940 B2
(45) Date of Patent: Mar. 2, 2021

(54) ARRANGEMENT AND METHOD FOR PREDICTING ROAD FRICTION WITHIN A ROAD NETWORK

(71) Applicant: VOLVO CAR CORPORATION, Gothenburg (SE)

(72) Inventors: Erik Israelsson, Gothenburg (SE); Nasser Mohammadiha, Gothenburg (SE); Ghazaleh Panahandeh, Gothenburg (SE)

(73) Assignee: VOLVO CAR CORPORATION, Gothenburg (SE)

( * ) Notice: Subject to any disclaimer, the term of this patent is extended or adjusted under 35 U.S.C. 154(b) by 861 days.

(21) Appl. No.: 15/424,246

(22) Filed: Feb. 3, 2017

(65) Prior Publication Data
US 2017/0236052 A1 Aug. 17, 2017

(30) Foreign Application Priority Data
Feb. 11, 2016 (EP) ..................... 16155263

(51) Int. Cl.
*G06N 3/04* (2006.01)
*G08G 1/01* (2006.01)
(Continued)

(52) U.S. Cl.
CPC .......... *G06N 3/0427* (2013.01); *G01N 19/02* (2013.01); *G01N 33/42* (2013.01); *G06N 3/08* (2013.01);
(Continued)

(58) Field of Classification Search
CPC ........ G06N 3/0427; G06N 3/08; G01N 19/02; G01N 33/42; G08G 1/0112
See application file for complete search history.

(56) References Cited

U.S. PATENT DOCUMENTS

| | | | |
|---|---|---|---|
| 7,248,958 B2 * | 7/2007 | Watanabe | B60T 8/1725 |
| | | | 701/1 |
| 9,187,099 B2 * | 11/2015 | Powers | G08G 1/0112 |

(Continued)

FOREIGN PATENT DOCUMENTS

| | | |
|---|---|---|
| EP | 2757539 A1 | 7/2014 |
| WO | 2010019045 A1 | 2/2010 |
| WO | 2013173911 | 11/2013 |

OTHER PUBLICATIONS

Jadranko Matusko, Ivan Petrovic, and Nedjeljko Peric, "Neural network based tire/road friction force estimation", Available online Jul. 2, 2007, Engineering Applications of Artificial Intelligence 21, pp. 442-456. (Year: 2007).*

(Continued)

*Primary Examiner* — Kamran Afshar
*Assistant Examiner* — Ying Yu Chen
(74) *Attorney, Agent, or Firm* — Brooks Kushman P.C.

(57) ABSTRACT

A system and method are described for predicting road friction using data from a fleet of connected vehicles. Each fleet vehicle includes a communication arrangement for reporting, to a back end system, floating car data sets, including a position of the vehicle, time data and data regarding determined road friction influencing parameters and a determined road friction associated with that position. The data sets are collected and aggregated in a central database, over a predetermined time period. A neural network computer is trained and validated, using aggregated data sets, to create a model to predict future road friction for a specific road network position or segment associated with that specific position. Once trained and validated, the neural network computer, upon receiving the same type of new, up to date, input data, uses the model to predict future road (Continued)

friction for that specific position or segment of the road network.

13 Claims, 2 Drawing Sheets

(51) Int. Cl.
*H04Q 9/00* (2006.01)
*G01N 19/02* (2006.01)
*G01N 33/42* (2006.01)
*G06N 3/08* (2006.01)
*G08G 1/00* (2006.01)

(52) U.S. Cl.
CPC ......... *G08G 1/0112* (2013.01); *G08G 1/0129* (2013.01); *G08G 1/0141* (2013.01); *G08G 1/205* (2013.01); *H04Q 9/00* (2013.01); *H04Q 2209/50* (2013.01); *H04Q 2209/826* (2013.01)

(56) References Cited

U.S. PATENT DOCUMENTS

| | | |
|---|---|---|
| 2008/0030370 A1 | 2/2008 | Doyle |
| 2011/0043377 A1 | 2/2011 | Mcgrath et al. |
| 2015/0154864 A1* | 6/2015 | Hainzlmaier ...... G08G 1/09626 340/905 |

OTHER PUBLICATIONS

Extended European Search Report for EP 16155263.3, Completed by the European Patent Office dated Aug. 17, 2016 All together 7 Pages.
Kangas et al., RoadSurf: a modelling system for predicting road weather and road surface conditions: Road weather model RoadSurf, Meteorological Applications, vol. 22, No. 3, Jan. 29, 2015, pp. 544-553, XP055570404, ISSN: 1350-4827.
European Patent Office, Office Action for corresponding European Application No. 16155263.3-1215, dated Mar. 22, 2019.
First Office Action for Chinese Application No. 201710076895.0, dated Dec. 2, 2020, 10 Pages.
U.S. Pat. No. 9,187,099B2, Non-Final Rejection dated Jan. 23, 2020.
U.S. Pat. No. 7,248,958B2, Non-Final Rejection dated Jan. 23, 2020.
WO2013173911A1.
U.S. 2008030370A1.
U.S. 2011043377A1.
WO2010019045A1.
EP2757539A1.

* cited by examiner

ARRANGEMENT AND METHOD FOR PREDICTING ROAD FRICTION WITHIN A ROAD NETWORK

CROSS-REFERENCE TO RELATED APPLICATIONS

This application claims foreign priority benefits under 35 U.S.C. § 119(a)-(d) to European patent application number EP 16155263.3, filed Feb. 11, 2016, which is incorporated by reference in its entirety.

TECHNICAL FIELD

The present disclosure relates to a system for predicting road friction using data from a fleet of connected vehicles equipped with respective positioning systems and one or more respective sensor systems capable of determining a plurality of road friction influencing parameters during travel within a road network the road friction within which is of interest.

The disclosure further relates to a method for predicting road friction using data from a fleet of connected vehicles equipped with respective positioning systems and one or more respective sensor systems capable of determining a plurality of road friction influencing parameters during travel within a road network the road friction within which is of interest.

The disclosure further relates to a connected vehicle, suitable to form part fleet of connected vehicles, the connected vehicle equipped with a positioning system and one or more respective sensor systems capable of determining a plurality of road friction influencing parameters during travel within a road network the friction of which is of interest.

BACKGROUND

It has been observed that dynamic variations in road friction over time typically depend on specific characteristics of different road segments that constitute a road network. In some road segments road surface ice will melt faster, e.g. if the road surface is freely exposed to sunlight. In other road segments road surface ice will develop more quickly during cold weather, e.g. if these road segments are located close to open water.

Attributes affecting road friction can be related to the shape of the landscape profile, to the geographical topology, to the geology. The number of parameters and the multitude of combinations possible make it difficult, but not impossible, to create analytical models to forecast road conditions, including road friction.

It has been proposed to create such analytical models to forecast road conditions, including road friction, however, creating such analytical models normally requires both specialized competence and understanding of how each of the relevant attributes affects road friction. Such analytical forecast models also require extensive input data describing the relevant characteristic of each road segment throughout the road network, e.g. knowledge of the geography and geology need to be included into the model. This requires data describing the road network in such terms. In order to accommodate for the unique characteristic of each road segment, developing such analytical models for each road segment of a road network will require a considerable manual effort.

However, since there exist today no feasible way to reliably collect the extensive input data describing the relevant characteristic of each road segment throughout a road network, and especially keeping it up to date with changed conditions the available data at its best only describes a present status of the road network. Changed road conditions may e.g. be that a forest adjacent a road segment could grow higher over time with longer shadows over the road, that will affect the development of low road friction, or conversely, logging operations could open up a previously shadowed road surface to sunlight. Consequently, this type of data will therefore be incomplete, especially with respect to changes, as described above. Thus, due to the incompleteness of the data, forecasts of road friction obtained from such data will inherently be flawed with uncertainty.

Thus there is a need for solutions to cost efficiently and more accurately conduct road friction forecasts without requiring the considerable manual effort as discussed above.

SUMMARY

Embodiments herein aim to provide an improved system for more accurately predicting road friction by forecasts models requiring less effort to create and maintain.

This is provided through a system for predicting road friction using data from a fleet of connected vehicles equipped with respective positioning systems and one or more respective sensor systems capable of determining a plurality of road friction influencing parameters during travel within a road network the road friction within which is of interest, where each respective vehicle in the fleet of connected vehicles comprises: a communication arrangement, arranged to communicate with a back end system to continuously report floating car data sets including a position of the connected vehicle within the road network, time data and data regarding determined road friction influencing parameters and a determined road friction associated with that position within the road network; and the system for predicting road friction further comprising: a central database, residing in the back end system, and arranged to collect the reported floating car data sets of the connected vehicles within the fleet and to aggregate in the central database a series of such floating car data sets over a predetermined time period; and a neural network computer arranged to be trained and validated, using the aggregated floating car data sets from the connected vehicles within the fleet, to create a model to predict future road friction for a specific position within the road network, using the aggregated floating car data sets from the connected vehicles within the fleet; and an optional data pre-processing arrangement, arranged to pre-process the floating car data sets to an appropriate structure should the data for the training and validation of the neural network computer not be structured appropriately by default; the neural network computer further arranged to, once trained and validated, receive the same type of new, up to date, input data and use the created model to predict future road friction, for a specific position within the road network or segment of the road network associated with that specific position.

According to a second embodiment it is provided that the floating car data sets from each respective vehicle in the fleet of connected vehicles include, but are not limited to, ambient temperature, wiper speed, air humidity, sun load, fog lights activation and detected actual road friction.

The provision of the floating car data sets including the above data provides for the inclusion of readily available data from existing vehicle systems and sensors.

According to a third embodiment it is provided that the communication arrangement is arranged to communicate with the back end system by an arrangement for wireless communication and in particular wireless data communication over a cellular network or similar.

The provision of having the communication arrangement arranged to communicate with the back end system as above provides for cost efficient use of readily available and proven communications infrastructure.

According to a fourth embodiment it is provided that each series of floating car data sets aggregated in the central database comprises all floating car data related to a specific position within the road network or segment of the road network associated with that specific position within a specified time window prior to a reported determined road friction related to the specific position within the road network or the segment of the road network associated with that specific position.

The provision of the series of floating car data sets aggregated in a central database comprising data as above provides an efficient way to, without manual effort, create and maintain up to date data describing a road network.

According to a fifth embodiment it is provided that the neural network computer further is arranged to be re-trained and re-validated to create an updated model to predict future road friction, with a re-training frequency based either on a pre-determined time interval or on the availability of a pre-determined amount of floating car data sets from the connected vehicles within the fleet collected and aggregated in the central database since a previous training and validation of the neural network computer.

The provision of having the neural network computer further arranged to be re-trained and re-validated as above provides an efficient way of ensuring the availability of an up to date model for forecasting road friction accounting for changed conditions in a road network.

According to a sixth embodiment it is provided that the neural network computer further is arranged to be trained and validated to create a model to predict future road friction, for a specific position within the road network, using, in addition to the aggregated floating car data sets from the connected vehicles within the fleet, data related to a time correlated weather forecast for the specific position within the road network or the segment of the road network associated with that specific position.

The provision of having the neural network computer further arranged to be trained and validated using also data related to a time correlated weather forecast as above provides for additionally increasing the quality of road friction predictions.

According to a seventh embodiment it is provided that the neural network computer further is arranged to be trained and validated to create a model to predict future road friction, for a specific position within the road network, using, in addition to the aggregated floating car data sets from the connected vehicles within the fleet, time correlated actual weather data for the specific position within the road network or the segment of the road network associated with that specific position.

The provision of having the neural network computer further arranged to be trained and validated using also time correlated actual weather data as above provides for yet further increasing the quality of road friction predictions.

Embodiments herein also aim to provide an improved method for more accurately predicting road friction.

Thus, according to an eight embodiment this is provided through a method for predicting road friction using data from a fleet of connected vehicles equipped with respective positioning systems and one or more respective sensor systems capable of determining a plurality of road friction influencing parameters during travel within a road network the road friction within which is of interest, where the method comprises: each respective vehicle in the fleet of connected vehicles communicating, using a communication arrangement, with a back end system to continuously report floating car data sets including a position of the connected vehicle within the road network, time data and data regarding determined road friction influencing parameters and a determined road friction associated with that position within the road network; and where the method further comprises: collecting to a central database, residing in the back end system, the reported floating car data sets of the connected vehicles within the fleet and aggregating in the central database a series of such floating car data sets over a predetermined time period; and training and validating a neural network computer, using the aggregated floating car data sets from the connected vehicles within the fleet, to create a model to predict future road friction for a specific position within the road network, based on the same type of new, up to date, input data; arranging the trained and validated the neural network computer to receive the same type of new, up to date, input data, and using the created model to predict future road friction, for a specific position within the road network or segment of the road network associated with that specific position.

According to a ninth embodiment it is provided that it further comprises including in the floating car data sets from each respective vehicle in the fleet of connected vehicles, at least, ambient temperature, wiper speed, air humidity, sun load, fog lights activation and detected actual road friction.

The provision of including in the floating car data sets the above data provides for the inclusion of readily available data from existing vehicle systems and sensors.

According to a tenth embodiment it is provided that it further comprises arranging the communication arrangement to communicate with the back end system by an arrangement for wireless communication and in particular wireless data communication over a cellular network or similar.

The provision of arranging the communication arrangement arranged to communicate with the back end system as above provides for cost efficient use of readily available and proven communications infrastructure.

According to an eleventh embodiment it is provided that it further comprises including in each series of floating car data sets to be aggregated in the central database all floating car data related to a specific position within the road network or segment of the road network associated with that specific position within a specified time window prior to a reported determined road friction related to the specific position within the road network or the segment of the road network associated with that specific position.

The provision of including in the series of floating car data sets to be aggregated in a central database data as above provides an efficient way to, without manual effort, create and maintain up to date data describing a road network.

According to a twelfth embodiment it is provided that it further comprises arranging the neural network computer to be re-trained and re-validated to create an updated model to predict future road friction, with a re-training frequency based either on a pre-determined time interval or on the availability of a pre-determined amount of floating car data sets from the connected vehicles within the fleet collected and aggregated in the central database since a previous training and validation of the neural network computer.

The provision of arranging the neural network computer to be re-trained and re-validated as above provides an efficient way of ensuring the availability of an up to date model for forecasting road friction accounting for changed conditions in a road network.

According to a thirteenth embodiment it is provided that it further comprises arranging the neural network computer to be trained and validated to create a model to predict future road friction, for a specific position within the road network, using, in addition to the aggregated floating car data sets from the connected vehicles within the fleet, data related to a time correlated weather forecast for the specific position within the road network or the segment of the road network associated with that specific position.

The provision of arranging the neural network computer to be trained and validated using also data related to a time correlated weather forecast as above provides for additionally increasing the quality of road friction predictions.

According to an fourteenth embodiment it is provided that it further comprises arranging the neural network computer to be trained and validated to create a model to predict future road friction, for a specific position within the road network, using, in addition to the aggregated floating car data sets from the connected vehicles within the fleet, time correlated actual weather data for the specific position within the road network or the segment of the road network associated with that specific position.

The provision of arranging the neural network computer to be trained and validated using also time correlated actual weather data as above provides for yet further increasing the quality of road friction predictions.

According to a final embodiment there is provided a connected vehicle, suitable to form part of a fleet of connected vehicles, the connected vehicle equipped with a positioning system and one or more respective sensor systems capable of determining a plurality of road friction influencing parameters during travel within a road network the friction of which is of interest, which comprises: a communication arrangement, arranged to communicate with a back end system to continuously report floating car data sets including a position of the connected vehicle within the road network, time data and data regarding determined road friction influencing parameters and a determined road friction associated with that position within the road network.

A vehicle, as above, is able to, in an efficient way, without manual effort, harvest and update data describing a road network useful for creating and validating models for predicting road friction according to embodiments of the system for predicting road friction as described herein and in accordance with at least some embodiments of the method for predicting road friction as described herein.

BRIEF DESCRIPTION OF THE DRAWINGS

In the following, embodiments herein will be described in greater detail by way of example only with reference to attached drawings, in which.

Still other features of embodiments herein will become apparent from the following detailed description considered in conjunction with the accompanying drawings. It is to be understood, however, that the drawings are designed solely for purposes of illustration and not as a definition of the limits hereof, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION

As required, detailed embodiments are disclosed herein. However, it is to be understood that the disclosed embodiments are merely exemplary and that various alternative forms may be employed. The figures are not necessarily to scale. Some features may be exaggerated or minimized to show details of particular components. Therefore, specific structural and functional details disclosed herein are not to be interpreted as limiting, but merely as a representative basis for teaching one skilled in the art.

In the near future more and more road vehicles $V_{1-n}$ will be able to detect road friction, low as well as high. Measured friction data from such vehicles $V_{1-n}$ can be collected in a remote database 6, also called cloud or cloud database, to gather a comprehensive description of the present state of road friction in a road network 3, i.e. on what road segments low road friction is occurring. Information on present road friction can be used in new safety related applications of road vehicles to further increase road safety.

A number of safety related road vehicle functions would benefit from a prognosis of a future status of road friction, not limited to the present status, i.e. a forecast estimating which road segments in a road network 3 can be expected to have low road friction in a close future.

Hence, the present disclosure proposes a solution such that data from a fleet of connected vehicles $V_{1-n}$, can be used to accurately and cost efficiently predict road friction for a specific position $P_1$-$P_n$ within a road network 3 or segment of a road network 3 associated with that specific position $P_1$-$P_n$, the road friction within which is of interest. It is based on the use of vehicle data $D_1$-$D_n$ from on board vehicle systems and sensors 2 of the fleet of connected vehicles $V_{1-n}$, aggregated during travels within the road network 3, in combination with a neural network computer 7, trained and validated using the aggregated data $D_1$-$D_n$ to create a model to predict future road friction.

It is proposed to use a robust input data pre-trained neural network computer 7 based system for such road friction prediction, this as the traditional type of computing model is inadequate to process and make sense of the volumes of information that is required for road friction prediction in a large and potentially complex road network 3.

Also, as some input data $D_1$-$D_n$ may be unstructured, a new computing model is needed in order to process and make sense of it. Such a new computing model is provided by cognitive computing systems, such as e.g. developed by IBM and others under US DARPA SyNAPSE (Systems of Neuromorphic Adaptive Plastic Scalable Electronics) project.

Rather than being programmed to anticipate every possible answer or action needed to perform a function or set of tasks in response to certain input signals, cognitive computing systems can process data and learn by experience, much in the same way humans do.

Machine Learning or Deep Learning is learning from known sample data or information by mining, induction, deduction, analogy and other methods to obtain the means and mechanisms of knowledge. Neural network computers 7 are based on artificial neural networks that intended to mimic the human brain structure and function as an information processing system.

Herein will be described solutions that proposes to use Floating Cars Data (FCD) both to create a model that can predict road friction and then as input data to the model in order to create up-to-date forecasts of road friction.

Figure 1:
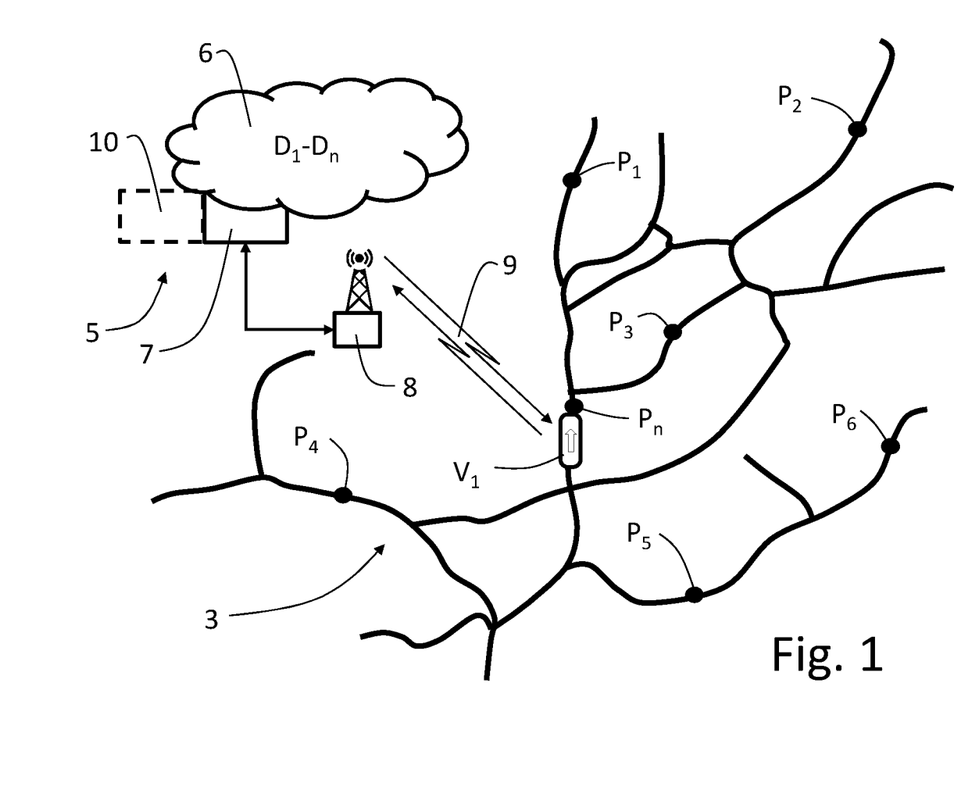
FIG. 1 is a schematic illustration of a system and method for predicting road friction according to embodiments herein.

Firstly will be described, and illustrated schematically in FIG. 1, a system for predicting road friction using data $D_1$-$D_n$ from a fleet of connected vehicles $V_{1-n}$ equipped with respective positioning systems 1, such as satellite based GPS (Global Positioning Systems) or similar, and one or more respective sensor systems 2 known in the art capable of and/or suitable for determining a plurality of road friction influencing parameters during travel within a road network 3 the road friction within which is of interest. For simplicity only one vehicle $V_1$ out of the fleet of connected vehicles $V_{1-n}$ is illustrated in FIG. 1 approaching the position $P_n$ in the road network 3.

Each respective vehicle in the fleet of connected vehicles $V_{1-n}$ comprises: a communication arrangement 4, such as an arrangement for wireless communication and in particular data communication over e.g. a cellular network or similar. The communication arrangement 4 is arranged to communicate with a back end system 5 to continuously report floating car data sets $D_1$-$D_n$, including a position $P_1$-$P_n$ of the connected vehicle within the road network 3, time data and data regarding determined road friction influencing parameters and a determined road friction, associated with that position $P_1$-$P_n$ within the road network 3. Actual road friction may e.g. be determined from traction control systems of a road vehicle (not shown). Road friction influencing parameters include, but are not limited to, ambient temperature, wiper speed, air humidity, sun load, fog lights activation.

The system for predicting road friction further comprises a central database 6, residing in the back end system 5, and arranged to collect the reported floating car data sets $D_1$-$D_n$ of the connected vehicles $V_{1-n}$ within the fleet and to aggregate in the central database 6 a series of such floating car data sets $D_1$-$D_n$ over a predetermined time period.

The central database 6 or cloud/cloud database, residing in the back end system 5, will receive a stream of floating car data $D_1$-$D_n$ from all connected vehicles $V_{1-n}$. Whenever a connected vehicle $V_{1-n}$ passes any given road segment, or position $P_1$-$P_n$, in the road network 3, new data will be available to the central database 6, so that the present status data related to that geographical position $P_1$-$P_n$ is updated. In this way, for any given position $P_1$-$P_n$ in the road network 3 there will be a stream of data $D_1$-$D_n$ describing the ever changing present status at that position $P_1$-$P_n$, e.g. temperature, sun load, rain or air humidity. Admittedly, such a data stream $D_1$-$D_n$ will be quasi-continuous and stochastic, since it will depend on the road traffic. There will be new data $D_1$-$D_n$ only when a connected vehicle $V_{1-n}$ happens to pass the road segment associated with that position $P_1$-$P_n$ and the data stream $D_1$-$D_n$ will be therefore be aperiodic since the time between connected vehicles $V_{1-n}$ will typically vary.

It is assumed that over time, a sufficient amount of connected vehicles $V_{1-n}$ will have passed the same road segment associated with that position $P_1$-$P_n$ and reported road friction influencing parameters and road friction detections, at different times, over days, weeks or months. Eventually, there will be an aggregated data set of such historical data series, that are all related to the same position $P_1$-$P_n$ or associated segment in the road network 3, and all including data for some time window prior to a friction measurement. This aggregated data set $D_1$-$D_n$ will provide sufficient input for the training and validation of a neural network computer 7 such that it, once trained and validated, will contain a model that will be able to predict future road friction based on the same type of new, up-to-date, input data, e.g. temperature, air humidity etc.

However, should the data for the training and validation of a neural network computer 7 not be structured appropriately by default, pre-processing to an appropriate structure will usually be required. In such cases an optional data pre-processing arrangement 10 may be arranged to pre-process the floating car data sets $D_1$-$D_n$ to an appropriate structure.

The distribution of the passing connected vehicles $V_{1-n}$ within the fleet during a desired interval, e.g., one hour, will be different over time. In other words, tens of floating car data sets $D_1$-$D_n$ might be received from 30 minutes ago until 15 minutes ago, while no floating car data sets $D_1$-$D_n$ may be received from 15 minutes ago until the current time. The missing floating car data sets $D_1$-$D_n$, i.e., the ones that have not been received during the desired interval, provide a complication in the prediction. It is thus appropriate to define a reference sampling rate for the floating car data sets $D_1$-$D_n$, which can be different for each road segment. This reference sampling rate should be set proportional to the number of connected vehicles $V_{1-n}$ passing a road segment. For example, assuming that ten connected vehicles $V_{1-n}$ within the fleet pass the given segment during one hour, then the number ten is referred to as the sampling rate. In structuring floating car data sets $D_1$-$D_n$, we need to take care of two cases: firstly that the number of passing connected vehicles $V_{1-n}$ within the fleet is larger than the sampling rate; and secondly that the number of passing connected vehicles $V_{1-n}$ within the fleet is less than the sampling rate. The latter case is referred to as the "missing-data" case. When there are more floating car data sets $D_1$-$D_n$ than the sampling rate, we need to downsample the floating car data sets $D_1$-$D_n$, i.e., only keep some of them at equal intervals so that at the end, the number of available floating car data sets $D_1$-$D_n$ is equal to the sampling rate. This is intuitive because the collected floating car data sets $D_1$-$D_n$ are highly correlated. The "missing-data" case is explained below.

Handling missing data for the case that the number of passing connected vehicles V-n within the fleet is less than the sampling rate is done as follows. The general approach to handle the missing data is to develop a function to fill in the missing data entries using all the other received floating car data sets $D_1$-$D_n$. Imputation methods based on K-nearest neighbor (K-nn) method and multi-layer perceptron imputation can be used to design such functions. In this case, we propose to use a very effective solution for this problem motivated by the observation that each set of floating cars data corresponds to measurements from the same set of parameters such as temperature, sun load etc. If no sets of floating cars data are available at a given time, we can use the sets of floating cars data from neighboring times to impute the missing elements. More precisely, an estimate for the missing sets of floating cars data is obtained as a weighted sum of all available floating car data sets $D_1$-$D_n$ in the given dataset, where the weights are set such that a higher weight is associated with the sets of floating cars data whose time-of-receipt is close to the time of the missing data. After estimating a value for the missing data, the missing part is replaced with the estimated quantity to obtain a dataset where the number of floating car data sets $D_1$-$D_n$ is exactly equal to the sampling rate.

It is possible that the available data from floating car data sets $D_1$-$D_n$ be heterogeneous, i.e., some entries might be real-valued parameters taking real values, while some other entries might only take discrete values. The temperature is an example for the first category while the wiper status, which can be only on or off, is an example for the second category. In this case, a pre-processing might be necessary to make the data heterogeneous, for example such that all the entries have zero mean.

After structuring the data, if required, there will be input data, obtained from the floating car data sets $D_1$-$D_n$. Hence, a neural network computer 7 is arranged to be trained and validated, using the aggregated floating car data sets $D_1$-$D_n$ from the connected vehicles $V_{1-n}$ within the fleet, to create a model to predict future road friction for a specific position $P_1$-$P_n$ within the road network 3, based on the same type of new, up to date, input data.

The neural network computer 7 is further arranged to, once trained and validated, receive the same type of new, up to date, input data, and use the created model to predict future road friction, for a specific position $P_1$-$P_n$ within the road network 3 or segment of the road network 3 associated with that specific position $P_1$-$P_n$. Hence will be output data, corresponding to the predicted future road friction. The, possibly structured, floating car data sets $D_1$-$D_n$ and the output data, corresponding to the predicted future road friction, make an input-output pair.

Since the data series are all related to a unique position $P_1$-$P_n$ or segment of the road network 3, it is understood that the neural network computer 7 will be uniquely trained to predict road friction for a specific location in the road network 3. Repeating the process for each unique position $P_1$-$P_n$ or road segment will lead to a model that can forecast road friction throughout the road network 3.

This complexity, training the neural network computer 7 for each road segment, is a consequence of the initial observation that road networks 3 are complex with respect to how a multitude of aspects affect the road friction development over time. It has to be emphasized that, eventually it is envisaged to be possible to perform model reduction to reduce the number of trained neural network computers 7 based on the similarity between different road segments.

Thus, the proposed solution will provide a forecast model for road friction without the need to design an advanced analytical model that accommodates for how all the relevant attributes effect prognosis of road friction for each individual road segment in the road network 3, a model based on a neural network computer 7 that forecasts road friction based on historical vehicle sensor 2 data.

It is noted that training of a neural network computer 7 can be a relatively costly operation with respect to the computer processing required. But, since the training has to be done just once to train the neural network computer 7 this is not a major concern. Once the neural network computer 7 is trained to predict road friction for a position $P_1$-$P_n$ or road segment, the forecasting operation, where new up-to-date floating cars data is applied to the forecast function, is relatively quick and inexpensive.

The selected type of neural network computer 7 could possibly require periodic data to be used as input for the training. In such case a relatively long period time could be used to accommodate for the aperiodic pattern of floating cars data. The window of the historical data series that defines each of the data sets that are used for training of the neural network computer 7, are then divided into sub periods (sub windows). Note that the same period time would be used for all the datasets to make it possible to combine them into a sufficient dataset, with the same period, to enable training of the neural network computer 7 for a specific position $P_1$-$P_n$ in the road network 3. To smoothen out the aperiodic pattern of floating cars data, any floating cars data within a period in the time window, prior to an actual road friction measurement, will be generalized to that whole period without respect to the exact point in time during the period that the data was measured by the connected vehicle $V_{1-n}$ and reported to the central database 6. Note that this is just one example of how the aperiodic floating cars data could be managed to support training of the neural network computer 7.

Through using time windows of different lengths, e.g., 1 h, 3 h or 5 h, to define the data series, it is possible to train a set of different forecast functions, all being a neural network computer 7 trained on one of the data series, e.g. 1 h, 3 h or 5 h, to create forecast functions with different time horizon, e.g. 1 h, 3 h or 5 h.

The trained neural network computer 7 can also be used to provide a function to aggregate multiple floating cars data, including friction detection data, to estimate the present road friction. Here, the time window could be thought of as set closer to 0 h, i.e., a "forecast for the present state". Other reference data measuring road friction can be used for the training, e.g., friction data from high quality road friction measurement units. One purpose of the estimation model is to relate the road friction as measured by the connected vehicles $V_{1-n}$ to the more accurate friction measurements. With such training, the estimation model will become more accurate in the estimation of road friction based on friction data measured by the connected vehicles $V_{1-n}$.

Since estimation of a present road friction, based on actual measurements of road friction, could be expected to be less affected by how the unique and different characteristics of road segments affect the dynamics of road friction over time, the neural network computer 7 function trained to estimate present road friction, based on road friction measurement from connected vehicles $V_{1-n}$, could be expected to be more generally applicable, i.e. constant over the whole road network 3. Hence the estimation function is different to the forecast function in that it could be generally applicable to the complete road network 3 whereas the forecast function will be unique to each road segment associated with a specific position $P_1$-$P_n$ in the road network 3.

According to some embodiments herein the floating car data sets $D_1$-$D_n$ from each respective vehicle $V_{1-n}$ in the fleet of connected vehicles include, but are not limited to, ambient temperature, wiper speed, air humidity, sun load, fog lights activation and detected actual road friction. Having the floating car data sets $D_1$-$D_n$ including the above data provides for the inclusion of readily available data from existing vehicle systems and sensors 2.

As mentioned above, according to yet some embodiments herein, the communication arrangement 4 is arranged to communicate with the back end system 5 by an arrangement for wireless communication and in particular wireless data communication over a cellular network 8 or similar, as illustrated by the broken arrows 9. This provides for cost efficient use of readily available and proven communications infrastructure.

Each series of floating car data sets $D_1$-$D_n$ aggregated in the central database 6, in accordance with embodiments herein, comprises all floating car data related to a specific position within the road network or segment of the road network associated with that specific position $P_1$-$P_n$, within a specified time window prior to a reported determined road friction related to the specific position $P_1$-$P_n$ within the road network 3 or the segment of the road network 3 associated with that specific position $P_1$-$P_n$. Thus, whenever a connected vehicle $V_{1-n}$ detects actual road friction, high or low, this is a chance to create a new data set that includes the series of all relevant historical data in the central database 6 for that specific position $P_1$-$P_n$ in the road network 3 and for some defined time window prior to the friction detection. Hereby is provided an efficient way to, without manual effort, create and maintain up to date data describing a road network 3.

In order to provide an efficient way of ensuring the availability of an up to date model for forecasting road friction accounting for changed conditions in a road network 3 is provided, according to embodiments herein, that the neural network computer 7 further is arranged to be re-trained and re-validated to create an updated model to predict future road friction. Re-training and re-validation is performed with a re-training frequency based either on a pre-determined time interval or on the availability of a pre-determined amount of floating car data sets $D_1$-$D_n$ from the connected vehicles $V_{1-n}$ within the fleet, collected and aggregated in the central database 6 since a previous training and validation of the neural network computer 7.

Automated re-training of the neural network computer 7 may be applied in order to update the neural network computer 7 based on more recent datasets for that road segment. This allows the solution to adapt to changed conditions, such as e.g. a forest growing higher over time with longer shadows over the road that would affect the development of low road friction. Re-training of the neural network computer 7 on new data would accommodate for such changes. Note that such training is agnostic regarding to what conditions have changed. Still the re-training will be able to accommodate for the changes. This is fundamentally different from an analytical function, which would be based on some model of how an aspect, such as shadows, would affect road friction. Re-training will not have to be done too frequently, since the changes to accommodate for are assumed to be slow processes, e.g. a forest grows slowly. Therefore, the cost of re-training the neural network computer 7 should not be a problem.

The operation of letting the trained neural network computer 7 calculate the forecast for road friction, given a set of up-to-date input data, is a much quicker operation than the training process of the neural network computer 7. This is a good thing since this is an operation that will be repeated much more often than the re-training, e.g. whenever new floating cars data are available in the central database 6, the road friction prognosis for that position $P_1$-$P_n$ or segment of the road network 3 can be updated.

In addition to floating cars data, available weather forecasts may be used as an input to the road friction prognosis function. It is natural to assume a close correlation between weather forecasts and the change of road friction over time, e.g. just as floating cars data regarding temperature measurements is relevant to the neural network computer 7 prognosis, it is natural to assume that there will be a similarly close correlation to temperature predictions in weather forecasts. Hence, it makes sense to include weather forecast data to the dataset used to train the neural network computer 7. Applied to the proposed solution, it means that in addition to the floating cars data, collected whenever a connected vehicle $V_{1-n}$ passes a position $P_1$-$P_n$ or road segment associated with that position $P_1$-$P_n$, the present weather forecast for that position $P_1$-$P_n$ or road segment is also sampled and included in the dataset used to train the neural network computer 7.

According to yet some embodiments, in order to additionally increase the quality of road friction predictions, the neural network computer 7 is further arranged to be trained and validated to create a model to predict future road friction, for a specific position $P_1$-$P_n$ within the road network 3, using, in addition to the aggregated floating car data sets $D_1$-$D_n$ from the connected vehicles $V_{1-n}$ within the fleet, data related to a time correlated weather forecast for the specific position $P_1$-$P_n$ within the road network 3 or the segment of the road network 3 associated with that specific position $P_1$-$P_n$.

However, it can be noted that weather forecasts do not always turn out to be correct. The actual future weather may turn out to be different than the forecasted future weather. Since all training of the neural network computer 7 is done on "historical data", the sampled "historical weather forecasts" could be replaced by the actual weather as it turned out to be, since this will be known at the time of the training. Since the data set used as input for the training of the neural network computer 7 includes data over a time window, ending at the time of friction detection data, the floating cars data describing the actual weather during the time window will be known, e.g. sampled as floating cars data, such as ambient temperature and wiper speed by the same connected vehicle that measured and sampled the road friction. This strategy could eliminate noise from incorrect historical weather forecasts to the training of the neural network computer 7. However, this strategy will obviously not be able to eliminate the error from new up-to-date forecasts. If errors in weather forecasts are expected to be systematic, which should normally not be the case, it could be wise to let the forecast error remain in the training data, i.e. not replacing it with the correct actual weather data, to train the neural network computer 7 to compensate for such systematically erroneous weather forecasts.

Thus, in order to yet further increase the quality of road friction predictions, according still further embodiments herein, it is provided that the neural network computer 7 further is arranged to be trained and validated to create a model to predict future road friction for a specific position $P_1$-$P_n$ within the road network 3, using, in addition to the aggregated floating car data sets $D_1$-$D_n$ from the connected vehicles $V_{1-n}$ within the fleet, time correlated actual weather data for the specific position $P_1$-$P_n$ within the road network 3 or the segment of the road network 3 associated with that specific position $P_1$-$P_n$.

Still further, the present disclosure also proposes an improved method for more accurately predicting road friction in a road network 3. This is provided through a method for predicting road friction, which will be described in more detail in the following with reference to the schematic illustration provided in FIG. 1. The method relies on using data from a fleet of connected vehicles equipped with respective positioning systems 1, such as a GPS, and one or more respective known sensor systems 2 capable of and/or suitable for determining a plurality of road friction influencing parameters during travel within a road network 3 the road friction within which is of interest, where the method comprises:

each respective vehicle in the fleet of connected vehicles $V_{1-n}$ communicating, using a communication arrangement 4, with a back end system 5 to continuously report floating car data sets $D_1$-$D_n$ including a position $P_1$-$P_n$ of the connected vehicle within the road network 3, time data and data regarding determined road friction influencing parameters and a determined road friction associated with that position $P_1$-$P_n$ within the road network 3;

and where the method further comprises:

collecting to a central database 6, residing in the back end system 5, the reported floating car data sets $D_1$-$D_n$ of the connected vehicles $V_{1-n}$ within the fleet and aggregating in the central database 6 a series of such floating car data sets $D_1$-$D_n$ over a predetermined time period; and training and validating a neural network computer 7, using the aggregated floating car data sets $D_1$-$D_n$ from the connected vehicles $V_{1-n}$ within the fleet, to create a model to predict future road friction for a specific position $P_1$-$P_n$ within the road network 3, based on the same type of new, up to date, input data; and optionally pre-processing the floating car data sets $D_1$-$D_n$ to an appropriate structure should the data for the training and validation of the neural network computer 7 not be structured appropriately by default; and arranging the trained and validated the neural network computer 7 to receive the same type of new, up to date, input data, and using the created model to predict future road friction, for a specific position $P_1$-$P_n$ within the road network 3 or segment of the road network 3 associated with that specific position $P_1$-$P_n$.

According to some embodiments the method further comprises including in the floating car data sets $D_1$-$D_n$ from each respective vehicle in the fleet of connected vehicles $V_{1-n}$, at least, ambient temperature, wiper speed, air humidity, sun load, fog lights activation and detected actual road friction. This provides for the inclusion of readily available data from existing vehicle systems and sensors 2.

Still further, according some embodiments the method further comprises arranging the communication arrangement 4 to communicate with the back end system by an arrangement for wireless communication and in particular wireless data communication over a cellular network 8 or similar, as illustrated by the broken arrows 9. This provides for cost efficient use of readily available and proven communications infrastructure.

In order to efficiently, without manual effort, create and maintain up to date data describing a road network 3, according to yet some embodiments herein, is provided that the method further comprises including in each series of floating car data sets $D_1$-$D_n$ to be aggregated in the central database 6 all floating car data related to a specific position $P_1$-$P_n$ within the road network 3 or segment of the road network 3 associated with that specific position $P_1$-$P_n$ within a specified time window prior to a reported determined road friction related to the specific position $P_1$-$P_n$ within the road network 3 or the segment of the road network 3 associated with that specific position $P_1$-$P_n$.

An efficient way of ensuring the availability of an up to date model for forecasting road friction, accounting for changed conditions in a road network 3, is, according to still some embodiments herein, provided through that the method further comprises arranging the neural network computer 7 to be re-trained and re-validated to create an updated model to predict future road friction, with a re-training frequency based either on a pre-determined time interval or on the availability of a pre-determined amount of floating car data sets $D_1$-$D_n$ from the connected vehicles $V_{1-n}$ within the fleet, collected and aggregated in the central database since a previous training and validation of the neural network computer 7.

Embodiments of the method for additionally increasing the quality of road friction predictions provides that it further comprises arranging the neural network computer 7 to be trained and validated to create a model to predict future road friction, for a specific position $P_1$-$P_n$ within the road network 3, using, in addition to the aggregated floating car data sets $D_1$-$D_n$ from the connected vehicles $V_{1-n}$ within the fleet, data related to a time correlated weather forecast for the specific position $P_1$-$P_n$ within the road network 3 or the segment of the road network 3 associated with that specific position $P_1$-$P_n$.

For yet further increasing the quality of road friction predictions, some embodiments herein provides that the method further comprises arranging the neural network computer 7 to be trained and validated to create a model to predict future road friction, for a specific position $P_1$-$P_n$ within the road network 3, using, in addition to the aggregated floating car data sets $D_1$-$D_n$ from the connected vehicles $V_{1-n}$ within the fleet, time correlated actual weather data for the specific position $P_1$-$P_n$ within the road network 3 or the segment of the road network 3 associated with that specific position $P_1$-$P_n$.

Figure 2:
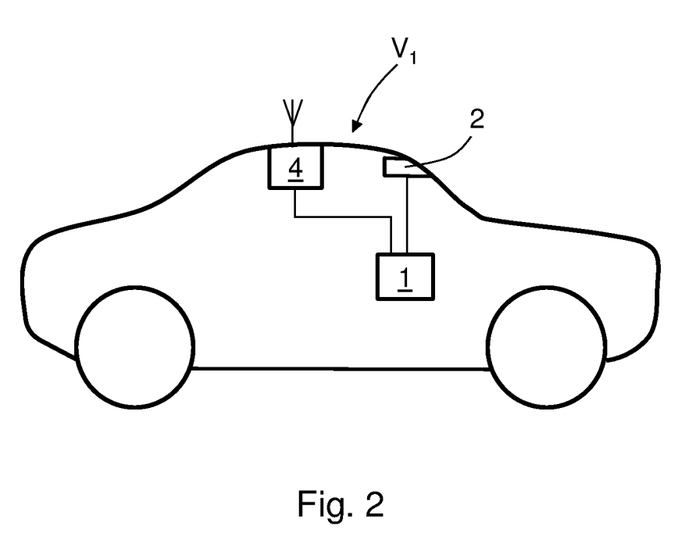
FIG. 2 is a schematic illustration of a connected vehicle suitable to form part of a fleet of connected vehicles in a system and method for predicting road friction according to embodiments herein.

Finally, the present disclosure also proposes a connected vehicle $V_1$, as illustrated schematically in FIG. 2, suitable to form part of a fleet of connected vehicles $V_{1-n}$, the connected vehicle $V_1$ equipped with a positioning system 1, such as a GPS, and one or more respective known sensor systems 2 capable of and/or suitable for determining a plurality of road friction influencing parameters during travel within a road network 3 the friction of which is of interest. The connected vehicle $V_1$ comprises a communication arrangement 4, arranged to communicate with a back end system 5 to continuously report floating car data sets $D_1$-$D_n$ including a position $P_1$-$P_n$ of the connected vehicle $V_1$ within the road network 3, time data and data regarding determined road friction influencing parameters and a determined road friction associated with that position $P_1$-$P_n$ within the road network 3.

A vehicle $V_1$, as above, is able to, in an efficient way, without manual effort, harvest and update data describing a road network 3, which data is useful for creating and validating models for predicting road friction according to embodiments of the system for predicting road friction as described herein and in accordance with embodiments of the method for predicting road friction as described herein.

It should be noted that the vehicle, positioning system 1, sensors 2, communication arrangement 4, back end system 5, central database 6, neural network computer(s) 7, and pre-processing arrangement 10 and/or any other arrangement, system, unit, module and/or device described herein may comprise one or more appropriately programmed processors and/or servers (e.g., one or more microprocessors including central processing units (CPU)) and associated memory, which may include stored operating system software and/or application software executable by the server(s) and/or processor(s) for controlling operation thereof and for performing the particular algorithms represented by the various functions and/or operations described herein, including interaction between and/or cooperation with each other. It should also be noted that the vehicle, positioning system 1, sensors 2, communication arrangement 4, back end system 5, database 6, neural network computer(s) 7, and pre-processing arrangement 10 may further comprise or be arranged or configured to cooperate with any type of storage device or arrangement known in the art, such as optical, solid state, disk and/or tape storage devices and controllers and/or one or more storage area networks, which may for example be used for storing data for central database 6. The vehicle, positioning system 1, sensors 2, communication arrangement 4, back end system 5, database 6, neural network computer(s) 7, and pre-processing arrangement 10 may further comprise any computer hardware and software and/or electrical hardware known in the art configured to enable communication therebetween, which may include cellular network 8 and/or other wireless networks.

The back end system 5, database 6, neural network computer(s) 7, and pre-processing arrangement 10 may be provided at a single or a central location or at multiple different locations. The method and system described herein may provide for distributed client-server computing involving the vehicle, cloud, positioning system 1, sensors 2, communication arrangement 4, back end system 5, database 6, neural network computer(s) 7, and pre-processing arrangement 10 over one or more networks 8 as described herein. In that regard, as previously noted, the back end system 5, database 6, neural network computer(s) 7, and pre-processing arrangement 10 may comprise a storage medium or device and one or more processors, which may comprise a local and/or remote server, having and/or for use with software and/or firmware that when executed by the one or more processors perform the functions and/or operations described herein. The computer executable instructions may comprise any type of neural network instructions, such as for creating, training and validating a neural network, and any type of instructions for implementing a database and/or a database management system for defining and/or managing a database as described herein. The computer executable instructions for implementing a database and/or a database management system may comprise any type of database instructions, such as instructions for creating, structuring, defining, indexing, acquiring, receiving, storing, adding, updating, deleting, searching, querying, fetching, retrieving, sorting, sending, returning, and/or otherwise defining, manipulating, managing and/or administering the database and/or data associated therewith.

The above-described embodiments may be varied within the scope of the following claims. Thus, while there have been shown and described and pointed out fundamental novel features of the embodiments herein, it will be understood that various omissions and substitutions and changes in the form and details of the devices illustrated, and in their operation, may be made by those skilled in the art. For example, it is expressly intended that all combinations of those elements and/or method steps which perform substantially the same function in substantially the same way to achieve the same results are equivalent. Moreover, it should be recognized that structures and/or elements and/or method steps shown and/or described in connection with any disclosed form or embodiment herein may be incorporated in any other disclosed or described or suggested form or embodiment as a general matter of design choice.

While exemplary embodiments are described above, it is not intended that these embodiments describe all possible forms of the disclosure. Rather, the words used in the specification are words of description rather than limitation, and it is understood that various changes may be made without departing from the spirit and scope of the disclosure. Additionally, the features of various implementing embodiments may be combined to form further embodiments of the disclosure.

What is claimed is:

1. A system for predicting road friction using data from a fleet of connected vehicles wherein each connected vehicle in the fleet is equipped with respective positioning systems and one or more respective sensor systems capable of determining a plurality of road friction influencing parameters during travel within a road network having a road friction of interest, each respective vehicle in the fleet of connected vehicles further having a communication arrangement configured to communicate with a back end system to continuously report floating car data sets including a position of the respective connected vehicle within the road network, time data and data regarding determined road friction influencing parameters and a determined road friction associated with that position within the road network, the system for predicting road friction comprising:
    a central database, residing in the back end system, and configured to collect the reported floating car data sets of the connected vehicles within the fleet and to aggregate in the central database a series of reported floating car data sets over a predetermined time period; and
    a neural network computer residing in the back end system and configured to be trained and validated, using the aggregated reported floating car data sets from the connected vehicles within the fleet, to create a model to predict future road friction for a specific position within the road network;
    wherein the neural network computer is further configured to, once trained and validated, receive further floating car data sets and use the created model to predict future road friction, for the specific position within the road network or segment of the road network associated with the specific position;
    wherein the neural network computer is further configured to be automatically re-trained and re-validated to create an updated model to predict future road friction and wherein automated re-training of the neural network computer updates the neural network computer based on datasets for a road segment reported after the neural network computer was last trained, with a re-training frequency based either on a pre-determined time interval or on availability of a pre-determined amount of reported floating car data sets from the connected vehicles within the fleet collected and aggregated in the central database since a previous training and validation of the neural network computer; and
    wherein each series of floating car data sets aggregated in the central database comprises all floating car data related to a specific position within the road network or segment of the road network associated with the specific position within a specified time window prior to a reported determined road friction related to the specific position within the road network or the segment of the road network associated with the specific position.

2. The system according to claim 1 wherein the reported floating car data sets from each respective vehicle in the fleet of connected vehicles comprise ambient temperature, wiper speed, air humidity, sun load, fog lights activation and determined actual road friction.

3. The system according to claim 1 wherein the communication arrangement is configured to communicate with the back end system by an arrangement for wireless communication over a network.

4. The system according to claim 1 wherein the neural network computer is further configured to be trained and validated to create a model to predict future road friction, for a specific position within the road network, using, in addition to the aggregated reported floating car data sets from the connected vehicles within the fleet, data related to a time correlated weather forecast for the specific position within the road network or the segment of the road network associated with the specific position.

5. The system according to claim 1 wherein the neural network computer is further configured to be trained and validated to create a model to predict future road friction, for a specific position within the road network, using, in addition to the aggregated reported floating car data sets from the connected vehicles within the fleet, time correlated actual weather data for the specific position within the road network or the segment of the road network associated with that specific position.

6. The system according to claim 1 wherein the back end system further comprises a pre-processing arrangement wherein, in response to the reported floating car data sets failing to conform to a particular data structure for the training and validation of the neural network computer, the pre-processing arrangement is configured to pre-process the reported floating car data sets to the particular structure.

7. A method for predicting road friction using data from a fleet of connected vehicles wherein each connected vehicle in the fleet is equipped with respective positioning systems and one or more respective sensor systems capable of determining a plurality of road friction influencing parameters during travel within a road network having a road friction of interest, each respective vehicle in the fleet of connected vehicles having a communication arrangement for communicating with a back end system to continuously report floating car data sets including a position of the respective connected vehicle within the road network, time data and data regarding determined road friction influencing parameters and a determined road friction associated with the position of the respective connected vehicle within the road network, the method comprising:
  collecting to a central database, residing in the back end system, the reported floating car data sets of the connected vehicles within the fleet and aggregating in the central database a series of the reported floating car data sets over a predetermined time period;
  training and validating a neural network computer, residing in the back end system, using the aggregated floating car data sets from the connected vehicles within the fleet, to create a model to predict future road friction for a specific position within the road network;
  configuring the trained and validated neural network computer to receive further floating car data sets and use the created model to predict future road friction for the specific position within the road network or segment of the road network associated with the specific position; and
  configuring the neural network computer to be automatically re-trained and re-validated to create an updated model to predict future road friction, wherein automated re-training of the neural network computer updates the neural network computer based on datasets for a road segment reported after the neural network computer was last trained, with a re-training frequency based either on a pre-determined time interval or on availability of a pre-determined amount of reported floating car data sets from the connected vehicles within the fleet collected and aggregated in the central database since a previous training and validation of the neural network computer; and
  including in each series of floating car data sets to be aggregated in the central database all floating car data related to a specific position within the road network or segment of the road network associated with that specific position within a specified time window prior to a reported determined road friction related to the specific position within the road network or the segment of the road network associated with the specific position.

8. The method according to claim 7 further comprising including in the reported floating car data sets from each respective vehicle in the fleet of connected vehicles, at least, ambient temperature, wiper speed, air humidity, sun load, fog lights activation and detected actual road friction.

9. The method according to claim 7 further comprising configuring the communication arrangement to communicate with the back end system by an arrangement for wireless communication over a network.

10. The method according to claim 7 further comprising configuring the neural network computer to be trained and validated to create a model to predict future road friction, for a specific position within the road network, using, in addition to the reported aggregated floating car data sets from the connected vehicles within the fleet, data related to a time correlated weather forecast for the specific position within the road network or the segment of the road network associated with the specific position.

11. The method according to claim 7 further comprising configuring the neural network computer to be trained and validated to create a model to predict future road friction, for a specific position within the road network, using, in addition to the reported aggregated floating car data sets from the connected vehicles within the fleet, time correlated actual weather data for the specific position within the road network or the segment of the road network associated with that specific position.

12. The method according to claim 7 further comprising, in response to the reported floating car data sets failing to conform to a particular data structure for the training and validation of the neural network computer, pre-processing the reported floating car data sets to the particular structure.

13. A vehicle configured to form part of a fleet of connected vehicles, the vehicle equipped with a positioning system and one or more respective sensor systems capable of determining a plurality of road friction influencing parameters during travel within a road network having a road friction of interest, the vehicle comprising:
  a communication arrangement configured to communicate with a back end system to continuously report floating car data sets including a position of the connected vehicle within the road network, time data and data regarding determined road friction influencing parameters and a determined road friction associated with the connected vehicle position within the road network;
  wherein a neural network computer, residing in the back end system, is configured to be trained and validated using the aggregated floating car data sets from the connected vehicles within the fleet to create a model to predict future road friction for a specific position with the road network;
  wherein the neural network computer is further configured to be automatically re-trained and re-validated to create an updated model to predict future road friction and wherein automated re-training of the neural network computer updates the neural network computer based on datasets for a road segment reported after the neural network computer was last trained, with a re-training frequency based either on a pre-determined time interval or on availability of a pre-determined amount of reported floating car data sets from the connected vehicles within the fleet collected and aggregated in the central database since a previous training and validation of the neural network computer;

wherein each series of floating car data sets aggregated in the central database comprises all floating car data related to a specific position within the road network or segment of the road network associated with the specific position within a specified time window prior to a reported determined road friction related to the specific position within the road network or the segment of the road network associated with the specific position.

* * * * *